United States Patent
Wiznia

(10) Patent No.: US 11,452,647 B2
(45) Date of Patent: Sep. 27, 2022

(54) CAST SAW TEMPERATURE SAFETY AND BURN REDUCTION SYSTEM

(71) Applicant: Osteomechanics LLC, Woodbridge, CT (US)

(72) Inventor: Daniel Wiznia, Woodbridge, CT (US)

(73) Assignee: Osteomechanics LLC, Woodbridge, CT (US)

( * ) Notice: Subject to any disclaimer, the term of this patent is extended or adjusted under 35 U.S.C. 154(b) by 142 days.

(21) Appl. No.: 16/586,572

(22) Filed: Sep. 27, 2019

(65) Prior Publication Data

US 2020/0100957 A1 Apr. 2, 2020

Related U.S. Application Data

(60) Provisional application No. 62/739,341, filed on Sep. 30, 2018.

(51) Int. Cl.
*A61F 15/02* (2006.01)
*B23D 59/00* (2006.01)
(Continued)

(52) U.S. Cl.
CPC .............. *A61F 15/02* (2013.01); *B23D 45/16* (2013.01); *B23D 59/001* (2013.01); *B23D 59/02* (2013.01); *B26D 7/088* (2013.01); *B26D 1/14* (2013.01)

(58) Field of Classification Search
CPC ....... A61F 15/02; B23D 45/16; B23D 45/165; B23D 59/00; B23D 59/001; B23D 59/008;
(Continued)

(56) References Cited

U.S. PATENT DOCUMENTS 4,148,236 A * 4/1979 Holoyen .............. B23Q 11/143
83/74
5,468,247 A * 11/1995 Matthai ................... A61F 15/02
30/339
(Continued)

FOREIGN PATENT DOCUMENTS

DE 20 2013 007 344 * 9/2013 ........... B23D 59/001

OTHER PUBLICATIONS

Stryker 940 Cast Cutter. Product information PDF brochure [online]. Published by Atlas International, 2019 [retrieved on Aug. 5, 2019]. Retrieved from the Internet: <URL: http://www.atlasprosales.com/v/vspfiles/downloadables/T-CC-940.pdf>.
(Continued)

*Primary Examiner* — Evan H MacFarlane
(74) *Attorney, Agent, or Firm* — Law Office of Matthew M Yospin; Matthew Yospin

(57) ABSTRACT

Apparatus is provided for a medical cutting device, specifically, a cast removal apparatus designed for the removal of orthopedic casts generally applied for immobilization, which apparatus comprises a temperature safety system and/or a burn reduction system. The use of any saw for cast removal creates a potential for patient discomfort and iatrogenic injury, including but not limited to burns which can leave unsightly scars and wound complications. The apparatuses presented comprise a housing for a temperature control system and motor, which motor can be controlled by the temperature control system to control a cast saw blade, with at least one temperature sensor to sense temperature information regarding at least one cutting region of the blade. The temperature information is used by the temperature control system to control the motor. The apparatuses presented comprise a burn reduction system with cast saw
(Continued)

blade coolant or lubricant and coolant or lubricant applicators.

2 Claims, 8 Drawing Sheets

(51) Int. Cl.
    *B23D 45/16*      (2006.01)
    *B26D 1/14*      (2006.01)
    *B23D 59/02*      (2006.01)
    *B26D 7/08*      (2006.01)

(58) Field of Classification Search
CPC .... B23D 59/02; B23D 59/025; B23D 61/006; B26D 7/08; B26D 7/088; A61B 17/14–15; B27B 19/006; B27B 19/008; B25F 5/008; B24B 23/04–046
See application file for complete search history.

(56) References Cited

U.S. PATENT DOCUMENTS

| | | | | |
|---|---|---|---|---|
| 7,431,682 | B2* | 10/2008 | Zeiler | B23B 45/00 483/9 |
| 10,953,509 | B2* | 3/2021 | Baratta | B23Q 17/00 |
| 10,993,859 | B2* | 5/2021 | Halanski | B27B 9/02 |
| 2016/0008897 | A1* | 1/2016 | McGehee | B23D 59/02 83/22 |
| 2019/0353535 | A1* | 11/2019 | Bonac | G01K 7/22 |
| 2021/0154758 | A1* | 5/2021 | Schmid | B23D 45/16 |

OTHER PUBLICATIONS

Stryker 940 Cast Saw Set. Product information webpage [online]. Published by Atlas International, 2019 [retrieved on Aug. 5, 2019]. Retrieved from the Internet: <URL: https://www.atlasprosales.com/Stryker_940_Cast_Saw_Set_p/t-cc-940-set6.htm>.

Stryker 940 Cast Removal System. Product information webpage [online]. Published by Medical Expo, 2019 [retrieved on Aug. 28, 2019]. Retrieved from the Internet: <URL: https://pdf.medicalexpo.com/pdf/stryker/cast-cutter/70192-169456.html#search-en-stryker-cast-cutter>.

DeSoutter Cast Cutter. Product information PDF brochure [online]. Published by Atlas International, 2019 [retrieved on Aug. 28, 2019]. Retrieved from the Internet: <URL: http://www.atlasprosales.com/v/vspfiles/downloadables/T-CC-5H.pdf>.

American Orthopaedic Cast Cutter. Product information webpage [online]. Published by BSN medical, 2019 [retrieved on Aug. 28, 2019]. Retrieved from the Internet: <URL: https://www.bsnmedical.us/products/orthopedics/category-product-search-o/fracture-management/cast-removal/american-cast-saw.html>.

Delta-Cast Saw; American Orthopaedic Cast Cutter Cast Saws; Power Blade Cast Saw Blades; Cast Saw Blades. Product information PDF brochure, pp. 42-44 [online]. Published by BSN medical, 2019 [retrieved on Aug. 28, 2019]. Retrieved from the Internet: <URL: https://www.bsnmedical.us/fileadmin/z-countries/0-USA_NEW/PDF_FILES/61861_RN_Orthopedics_Catalog.pdf>.

* cited by examiner

CAST SAW TEMPERATURE SAFETY AND BURN REDUCTION SYSTEM

FIELD OF THE INVENTION

The presently disclosed subject matter relates to providing apparatus for cast saws, and more particularly, to apparatus for a cast saw temperature safety system and cast saw burn reduction system.

BACKGROUND OF THE INVENTION

Immobilization is considered essential for the proper healing of broken bones and other internal trauma, and immobilization is typically achieved with the use of orthopedic casts. Removal of orthopedic casts is typically difficult by design, so that a cast functions effectively to immobilize the body part that needs to be immobilized. Cast saws are frequently used to remove casts, and oscillating saw blades are preferred, in which the cast saw blade oscillates within a range of typically a few millimeters, reducing the risk of cuts to the patient, provided that any skin contacted by the blade is mobile. If the skin can move with the cast saw blade as the blade oscillates, the skin is unlikely to be cut; if the skin is in a less-mobile region of the body, such as the skin over a bony prominence, the skin is more likely to be cut.

Conventionally, the use of an oscillating saw or non-oscillating saw for cast removal creates a potential for patient discomfort and for iatrogenic injury, such as burns and abrasions resulting from the heat created by frictional forces between the cast saw blade and the cast material. Often, thick casts are required or chosen to immobilize the injured area, and cutting through thick casts heats a cast saw blade and leads to increased risk of burns, as well as abrasions. Casts may be inadequately padded, which also increases the risk of injury after a saw blade has cut through the more rigid exterior cast material. Additionally, dull saw blades and improper user technique of cast saws can lead to second and third degree burns. Saw burns can leave unsightly scars and wound complications. There also exist types of shears for cutting orthopedic casts, but they carry other risks of injury.

Conventional cast saws generally do not provide information on or monitor the temperature of the cast saw blade. In conventional cast saws with oscillating blades, only a relatively small portion of the blade is used as a cutting region at a time. As that portion of the blade dulls, a user may loosen, rotate, and re-tighten the blade to use a sharper portion of the blade as the active cutting region, provided the blade comprises sufficiently distinct cutting regions—not all blades are circular, and some are not intended to be rotated. But, without a temperature indication, the user may not know that the blade is dull or otherwise susceptible to being overheated and should be cooled or rotated or replaced.

With cast saws, a hot blade can indicate that the blade is cutting through thick material, or that the blade is dull, or that when cutting a fiberglass cast, the resin or polymer epoxy typically used with the fiberglass material is sticking to the blade (often because it isn't fully dried). The resin or epoxy can adhere to the blade cutting region, boosting friction between the cast saw blade and the cast. Any of these can lead to a rise in the temperature of the blade, and without temperature information about the blade, the user may not know that the blade needs to be rotated or cooled to reduce the risk of injury to the patient.

Prior art devices exist for removing orthopedic casts, such as types of shears and scissor-type cutting devices, as well as cast saws, including but not limited to models from Stryker, DeSoutter, American Orthopaedic, and Delta-Cast, examples of which are provided in the Information Disclosure Statement accompanying this application, and all of which share the shortcomings of the prior art which the present invention seeks to solve. The prior art does not allow a user to control the motion and oscillation speed of a cast removal saw based on the temperature of one or more cutting regions of a cast saw blade, with the possibility of automatic feedback and programmed modes of operation, or lubrication or coolant, to lower or remove the risk to the patient of burns.

SUMMARY OF THE INVENTION

The present invention meets all these needs, by disclosing apparatus for a cast saw temperature safety system that provides monitoring and control of the cast blade for temperature, and by disclosing apparatus for a burn reduction system that lowers the temperature of the cast saw blade at one or more cutting regions of the cast saw blade. The present invention addresses the problem of the prior art with regard to cast saw burns, by providing control of the cast saw blade to keep the temperature of one or more cutting regions of the blade at or below a specified temperature range, and by providing a burn reduction system for cooling the cutting region of the cast saw blade. The present invention may also provide for control over the cast saw blade oscillation speed, because by slowing or speeding the oscillations of the cast saw blade the control system can effectively reduce the frictional forces between the cast saw blade and the orthopedic cast, and thus allow the temperature of a cutting region of the cast saw blade to lower, or allow the temperature to rise if the temperature is below an allowable threshold, providing additional benefits with regard to preventing cast saw burns.

The present invention addresses the problems of the prior art, which do not present apparatus for cast saw blade temperature monitoring and blade oscillation speed control for patient safety, by lowering the risk to the patient of injuries from burns. The temperature information provided by the present invention can indicate that the cutting region of the blade is dull, therefore alerting the user that the blade should be rotated (typically, by loosening, rotating, and re-tightening the blade, with blades which can be rotated). The temperature information may indicate that the blade is cutting thick cast material, or that a resin or polymer epoxy used in the fiberglass cast sticking to the blade, gumming up the blade and making it dull or otherwise unable to cut the cast material, which may suggest other approaches or caution in cutting the cast material.

The present invention addresses the problems of the prior art, which do not present burn reduction systems for lowering and controlling the temperature of the cutting region of the cast saw blade through application of a coolant to reduce the temperature of the cast saw blade, or where the coolant may be a lubricant to reduce friction between the cast saw blade and the cast and thus reduce the temperature of the cast saw blade.

In one aspect, the present invention comprises a cast saw blade, which cast saw blade comprises a plurality of cutting regions; a cast saw arbor, to which cast saw arbor the cast saw blade is attached; a cast saw motor, which cast saw motor is operably connected to the cast saw arbor; a cast saw body enclosing the cast saw motor, and to which cast saw body a plurality of temperature sensors is attached; and a temperature control system, which controls the cast saw motor to oscillate; wherein the plurality of temperature sensors convey temperature information to the temperature control system, which temperature information may comprise a plurality of temperature readings with one or more readings for each of one or more cutting regions of the cast saw blade; and wherein the temperature control system is configured to process the temperature information to determine if the temperature of the cast saw blade at a cutting region of the cast saw blade is at or above a threshold temperature.

In one aspect, the present invention comprises a cast saw blade, which cast saw blade comprises a plurality of cutting regions; a plurality of temperature sensors; a cast saw arbor, to which cast saw arbor the cast saw blade is attached; a cast saw motor, which cast saw motor is operably connected to the cast saw arbor; a cast saw body enclosing the cast saw motor; and a temperature control system, which controls the cast saw motor oscillation rate.

In one aspect of the present invention, the temperature control system on the cast saw body.

In one aspect of the present invention, the temperature control system is enclosed in the cast saw body.

In one aspect of the present invention, the plurality of temperature sensors is mounted to the cast saw body in a fixed manner.

In one aspect of the present invention, the plurality of temperature sensors is mounted to the cast saw body movably.

In one aspect of the present invention, the plurality of temperature sensors is embedded in the cast saw blade, or is external to and affixed to the cast saw blade.

In one aspect of the present invention, a connection between the plurality of temperature sensors and the temperature control system is achieved with wires running through the cast saw arbor or external to the cast saw arbor.

In one aspect of the present invention, a connection between the plurality of temperature sensors and the temperature control system is achieved with a wireless connection.

In one aspect of the present invention, the plurality of temperature sensors comprise one or more selected from a list comprising thermocouples, resistive temperature devices, thermistors, infrared radiators, lasers, bimetallic devices, liquid expansion devices, optical sensors, fiber Bragg grating optical sensors or other distributed Bragg reflector, thermowells, resistance thermometer, resistance temperature detectors, digital thermal imaging, infrared temperature measurement, or change-of-state devices.

In one aspect of the present invention, the plurality of temperature sensors convey temperature information to the temperature control system, which temperature information may comprise a plurality of temperature readings with one or more reading for each of one or more cutting regions of the cast saw blade; and wherein the temperature control system is configured to process the temperature information to determine if the temperature of the cast saw blade at a cutting region of the cast saw blade is at or above a threshold temperature.

In one aspect of the present invention, the temperature control system is configured to provide one or more warnings regarding the temperature of the cast saw blade.

In one aspect of the present invention, the cast saw temperature safety system further comprises an accelerometer, which accelerometer generates a plurality of orientation information.

In one aspect, the present invention comprises a method of controlling the operation of a cast saw temperature safety system, which cast saw temperature safety system comprises a cast saw blade comprising a plurality of cutting regions, a plurality of temperature sensors, a cast saw arbor to which the cast saw blade is attached, a cast saw motor operably connected to the cast saw arbor, a cast saw body enclosing the cast saw motor, and a temperature control system which controls the cast saw motor to oscillate, the method comprising: the cast saw temperature safety system having a temperature threshold for the plurality of cutting regions; the cast saw temperature safety system monitoring temperature information for each of one or more of the plurality of cutting regions; the temperature control system sending a control signal to the cast saw motor; and the temperature control system operating to slow or stop the cast saw blade if one or more of the cutting regions reaches or exceeds a temperature threshold.

In one aspect of the present invention, the temperature control system modifies the oscillation speed of the cast saw blade to prevent the cast saw blade from reaching a temperature threshold.

In one aspect of the present invention, a user can set a maximum safe temperature threshold.

In one aspect of the present invention, the temperature control system decreases the oscillation speed of the cast saw blade as the cast saw blade temperature increases, based on the temperature information from the plurality of temperature sensors, and the temperature control system increases the oscillation speed of the cast saw blade as the cast saw blade temperature decreases.

In one aspect of the present invention, the temperature control system allows the cast saw blade to oscillate at the highest oscillation speed possible without the cast saw blade temperature reaching or exceeding a maximum temperature threshold.

In one aspect of the present invention, the temperature control system controls the cast saw blade oscillations to be continuous or intermittent.

In one aspect of the present invention, the temperature control system controls the cast saw blade at any of a plurality of discrete oscillation speeds selectable by a user.

In one aspect of the present invention, the temperature control system provides one or more warnings to a user.

In one aspect of the present invention, the cast saw temperature safety system further comprises a plurality of strain gauges, and wherein the temperature control system operating to slow or stop the cast saw blade if one or more of the cutting regions reaches or exceeds a temperature threshold, does not operate to slow or stop the cast saw blade if the one or more of the cutting regions that reaches or exceeds a temperature threshold is not the region that is actively cutting, as determined by a plurality of strain information from the plurality of strain gauges.

In one aspect of the present invention, the cast saw temperature safety system further comprises an accelerometer, and wherein the temperature control system determines that the one or more of the cutting regions that reaches or exceeds a temperature threshold is not the region that is actively cutting based on a plurality of orientation information from the accelerometer.

In one aspect, the present invention comprises a cast saw burn reduction system, comprising: a cast saw blade, which cast saw blade comprises a plurality of cutting regions; a cast saw arbor, to which cast saw arbor the cast saw blade is attached; a cast saw motor, which cast saw motor is operably connected to the cast saw arbor; a cast saw body enclosing the cast saw motor; a coolant; a coolant reservoir; a reservoir cap; a coolant tube, which coolant tube transports coolant from the coolant reservoir to the cast saw blade; a coolant applicator; a coolant pump; a coolant control dial; at least one coolant intake; and a coolant control system, which coolant control system is connected to a plurality of coolant applicators; and wherein the coolant control system is used to cool and/or lubricate the cast saw blade so as to lower the temperature of the cast saw blade at one or more cutting regions of the cast saw blade.

In one aspect, the present invention comprises a cast saw burn reduction system, comprising: a cast saw blade, which cast saw blade comprises a plurality of cutting regions; a cast saw arbor, to which cast saw arbor the cast saw blade is attached; a cast saw motor, which cast saw motor is operably connected to the cast saw arbor; a cast saw body enclosing the cast saw motor; a coolant and coolant components; and wherein the burn reduction system allows for a user to control or cause to be released or applied onto or at the cast saw blade the coolant.

In one aspect of the present invention, the coolant components comprise one or more of the following; a coolant reservoir, a reservoir cap, a coolant, a coolant tube, a coolant pump, a plurality of coolant applicators, a coolant control dial, and a coolant intake; and wherein the coolant tube transports coolant from the coolant reservoir to the cast saw blade.

In one aspect of the present invention, the coolant may be released at or onto a plurality of locations on the cast saw blade, which locations may be at or near an active cutting region of the cast saw blade.

In one aspect of the present invention, the burn reduction system may be programmed to release or apply coolant automatically at or onto a plurality of locations on the cast saw blade.

In one aspect of the present invention, the coolant may be a coolant for evaporative cooling of the cast law blade.

In one aspect of the present invention, the coolant may be for convective heat transport away from the cutting region of the cast saw blade.

In one aspect of the present invention, the coolant for convective heat transport is blown at and over the surface of the cast saw blade.

In one aspect of the present invention, the coolant is a lubricant that serves to lower the temperature of at least one cutting region of the cast saw blade by reducing friction between the cast saw blade and the cast.

In one aspect of the present invention, more than one type of coolant is applied to the cutting region of the cast saw blade.

In one aspect of the present invention, the coolant tube may split into one or more branches or segments for each side of the cast saw blade so that the coolant may be applied to one or both sides of the cast saw blade.

In one aspect of the present invention, the coolant tube may comprise a plurality of discrete tubes or items for transport of one or more coolants.

In one aspect of the present invention, the user is able to direct the coolant onto a desired location or locations on the cast saw blade.

In one aspect of the present invention, the plurality of coolant applicators comprise a sponge-like material that can absorb, transport, and release a fluid coolant in contact with or in close proximity to the saw blade.

In one aspect of the present invention, the coolant pump may be a manually actuated component.

In one aspect of the present invention, the coolant pump may be an electrically actuated component.

In one aspect, the present invention comprises a method of controlling the operation of a cast saw burn reduction system, which cast saw burn reduction system comprises a cast saw blade comprising a plurality of cutting regions, a cast saw arbor to which the cast saw blade is attached, a cast saw motor operably connected to the cast saw arbor, a cast saw body enclosing the cast saw motor, and a coolant control system, which controls coolant application to the cast saw blade, the method comprising: the cast saw burn reduction system having a coolant pump that impels or pushes a coolant through a coolant tube and a plurality of coolant applicators at the cast saw blade; the cast saw burn reduction system having a coolant control dial to control the quantity of the coolant that is applied per actuation of the coolant pump; and the coolant control system operating under the control of a user or programmatically.

In one aspect of the present invention, the coolant pump impels or pushes the coolant from the coolant reservoir.

In one aspect of the present invention, the user may use the coolant control dial to control the aperture of the plurality of coolant applicators, or to control the pressure in the coolant reservoir, or to control the pressure of the coolant pump.

In one aspect of the present invention, the burn reduction system is used in conjunction with a temperature control system and the coolant control system actuates the coolant pump to apply coolant to the cast saw blade when the temperature control system indicates that a temperature information is at or above a certain threshold value for the temperature of a cutting region of the cast saw blade.

These aspects of the present invention, and others disclosed in the Detailed Description of the Drawings, represent improvements on the current art. This summary is provided to introduce a selection of concepts in a simplified form that are further described below in the Detailed Description of the Drawings. This Summary is not intended to identify key features or essential features of the claimed subject matter, nor is it intended to be used to limit the scope of the claimed subject matter.

BRIEF DESCRIPTION OF THE DRAWINGS

The foregoing summary, as well as the following detailed description of various embodiments, is better understood when read in conjunction with the appended drawings. For the purposes of illustration, the drawings show exemplary embodiments; but the presently disclosed subject matter is not limited to the specific methods and instrumentalities disclosed. In the drawings, like reference characters generally refer to the same components or steps of the device throughout the different figures. Elements of the exemplary embodiments in the drawings are shown for simplicity and clarity, and have not necessarily been drawn to scale. For example, the dimensions of some of the elements in the drawings may be exaggerated or diminished relative to other elements to help improve understanding of various embodiments. Additionally, common but well-understood elements that are useful or necessary in a commercially feasible embodiment may not be depicted, in order to facilitate a clearer view of one or more embodiments of the present invention. In the following detailed description, various embodiments of the present invention are described with reference to the following drawings, in which.

DETAILED DESCRIPTION OF THE DRAWINGS

Figure 1:
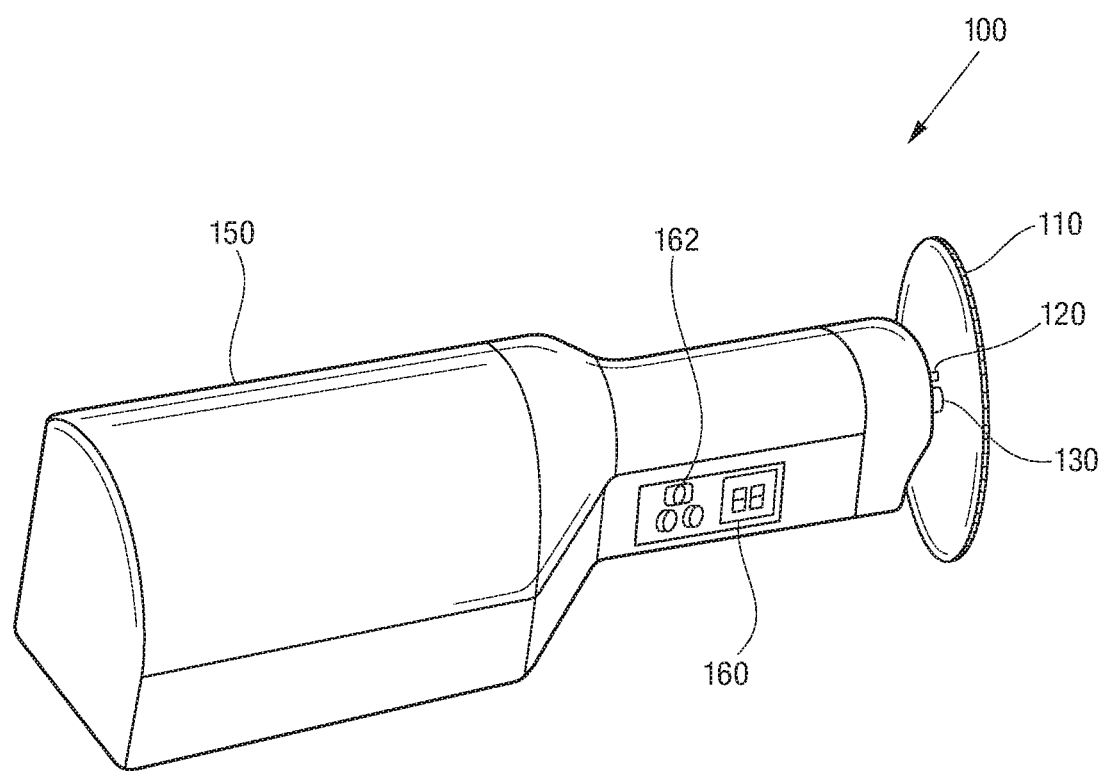
FIG. 1 shows a perspective view of an embodiment of the apparatus of the present invention.
Figure 2:
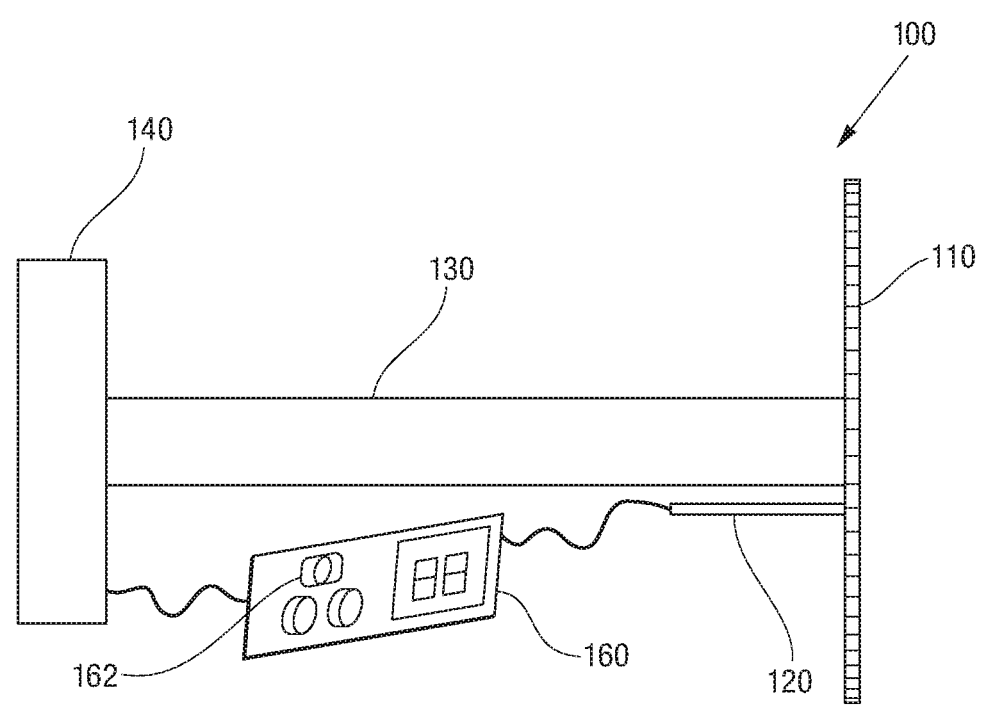
FIG. 2 shows a side elevation view of a simplified schematic portion of an embodiment of the apparatus of the present invention.
Figure 3:
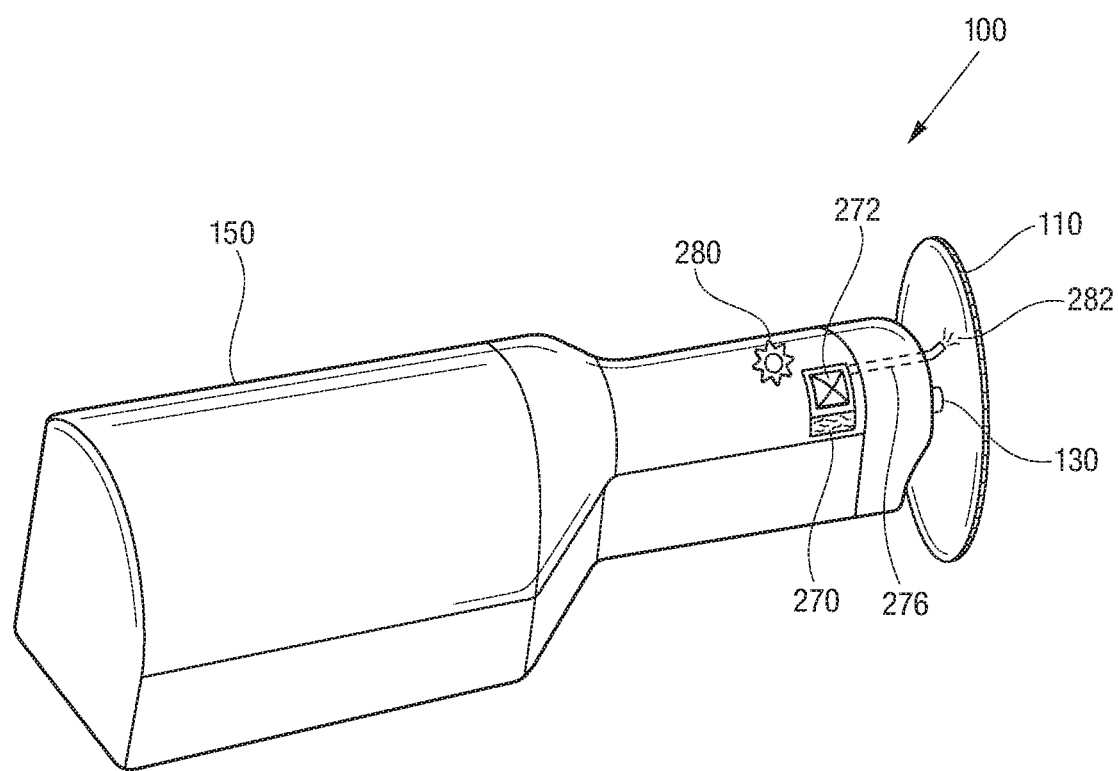
FIG. 3 shows a perspective view of an embodiment of the apparatus of the present invention.
Figure 4:
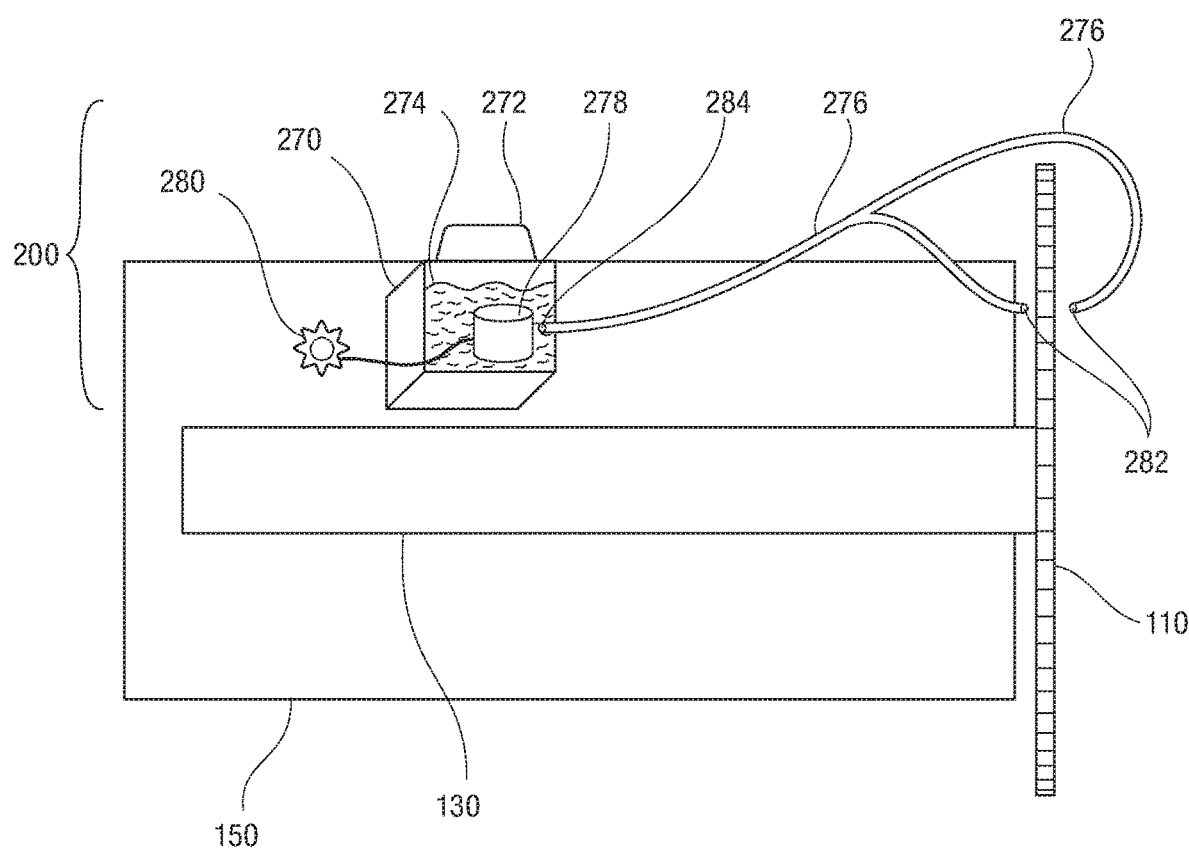
FIG. 4 shows a side elevation view of a simplified schematic portion of an embodiment of the apparatus of the present invention.

The presently disclosed invention is described with specificity to meet statutory requirements. But, the description itself is not intended to limit the scope of this patent. Rather, the claimed invention might also be embodied in other ways, to include different steps or elements similar to the ones described in this document, in conjunction with other present or future technologies. Moreover, although the term "step" or similar terms may be used herein to connote different aspects of methods employed, the term should not be interpreted as implying any particular order among or between various steps herein disclosed unless and except when the order of individual steps is explicitly described.

In the following description, numerous specific details are set forth to provide a thorough understanding of the invention. But, the present invention may be practiced without these specific details. Structures and techniques that would be known to one of ordinary skill in the art have not been shown in detail, in order not to obscure the invention. Referring to the figures, it is possible to see the various major elements constituting the apparatus and methods of use of the present invention.

The present invention comprises a novel cast saw temperature safety system 100, for use by a user 300 to cut an orthopedic cast 310 on a patient 320, or for other cutting tasks. With reference to FIGS. 1, 2, 5, and 8, the cast saw temperature safety system 100 comprises a cast saw blade 110, a plurality of temperature sensors 120, a cast saw arbor 130 (meaning an axis or shaft supporting a rotating part), a cast saw motor 140, a cast saw body 150, and a temperature control system 160. The cast saw body 150 encloses the cast saw motor 140, and the temperature control system 160 may be, it has been found advantageous, on and/or enclosed in the cast saw body 150. The cast saw motor 140 is operably connected to the cast saw arbor 130, to which cast saw arbor 130 the cast saw blade 110 is attached. The cast saw motor 140 may be directly connected to the cast saw arbor 130, or the cast saw motor 140 may perform complete revolutions, but be attached to a device or element which translates those complete revolutions into oscillations such that the cast saw arbor 130 oscillates. The temperature control system 160 controls the cast saw motor 140 oscillation rate, and thus controls the cast saw blade 110 oscillation rate. The plurality of temperature sensors 120 may be mounted to the cast saw body 150 in a fixed manner, or may be mounted to the cast saw body 150 movably, such that the plurality of temperature sensors 120 may be repositioned relative to the cast saw blade 110.

Figure 5:
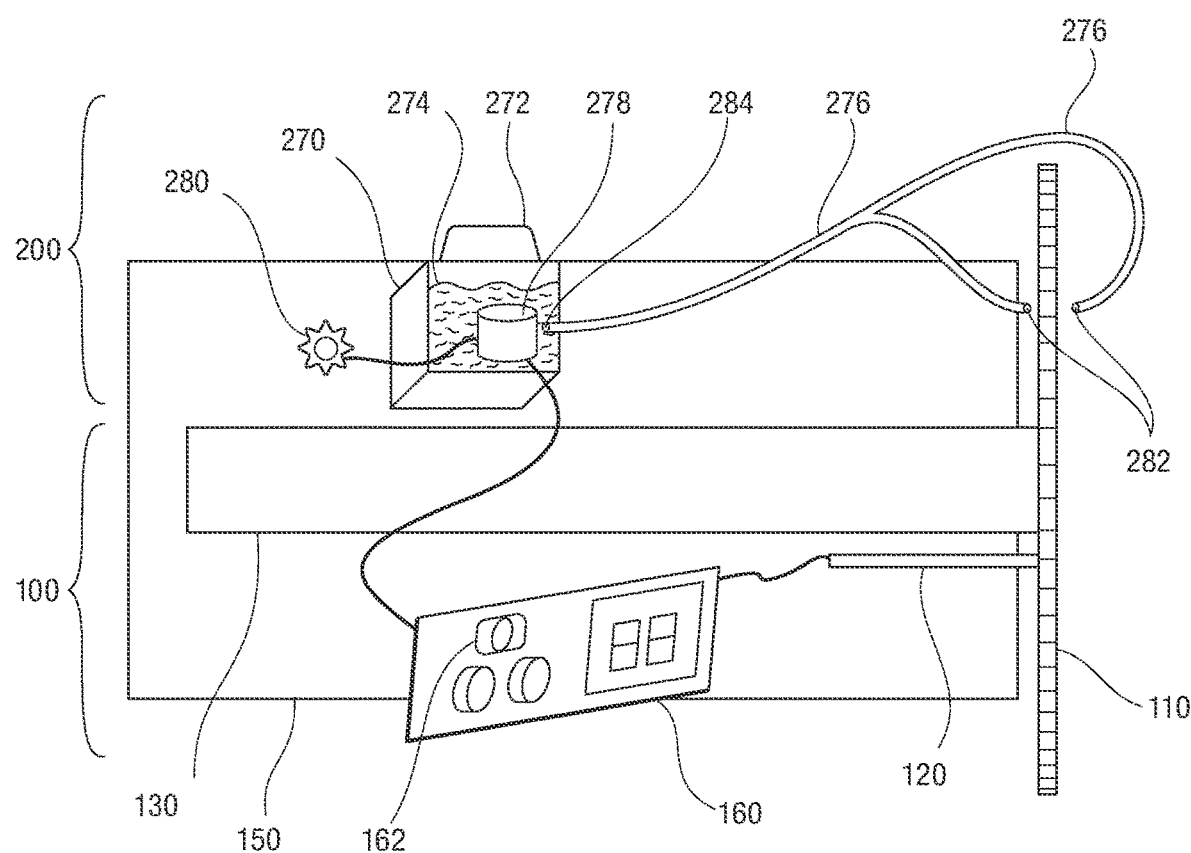
FIG. 5 shows a side elevation view of a simplified schematic portion of an embodiment of the apparatus of the present invention.
Figure 6:
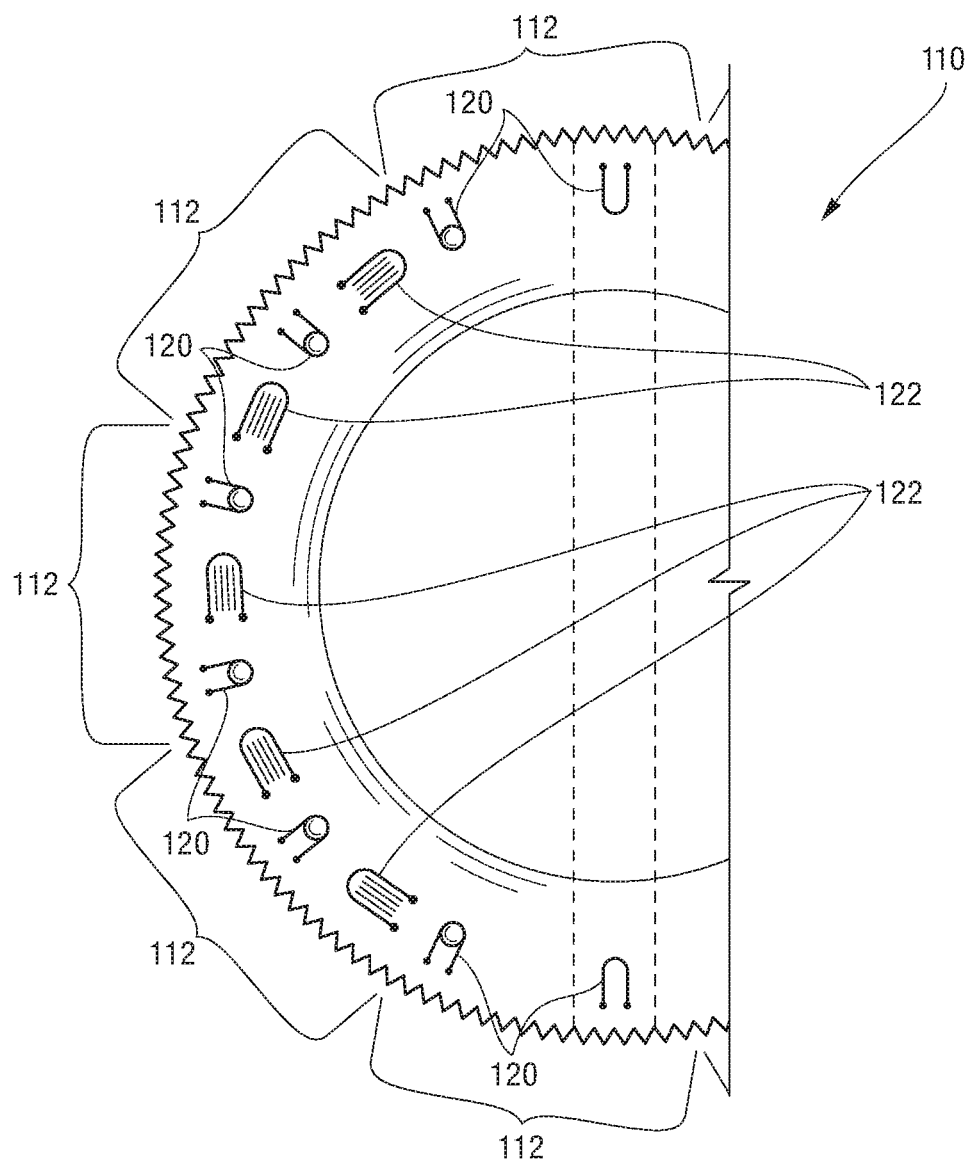
FIG. 6 shows an exemplary cast saw blade of an embodiment of the apparatus of the present invention in perspective and cross-sectioned along a diameter of the blade.

With reference to FIG. 6 and FIGS. 1, 2, and 5, the plurality of temperature sensors 120 may be embedded in the cast saw blade 110, in which case a connection between the plurality of temperature sensors 120 and the temperature control system 160 may be achieved with wires running through the cast saw arbor 130 or external to the cast saw arbor 130, or the connection between the plurality of temperature sensors 120 and the temperature control system 160 may be achieved with a wireless connection of a type now known or later invented, including but not limited to a Bluetooth, Wi-Fi, or other near-field communications protocol. The plurality of temperature sensors 120 may be external to and affixed to the cast saw blade 110, as shown in FIG. 6.

Figure 7:
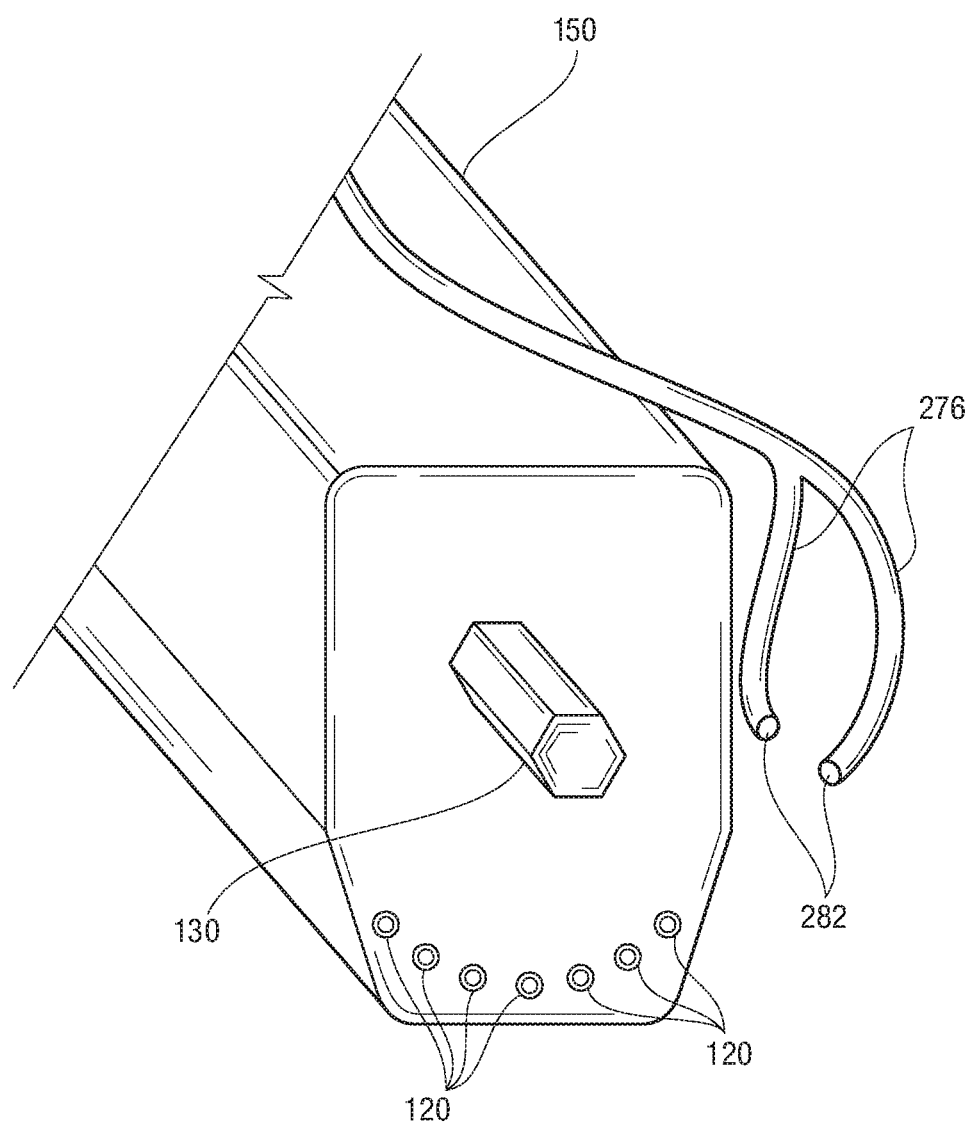
FIG. 7 shows a front perspective view of an embodiment of the apparatus of the present invention, with the blade removed.
Figure 8:
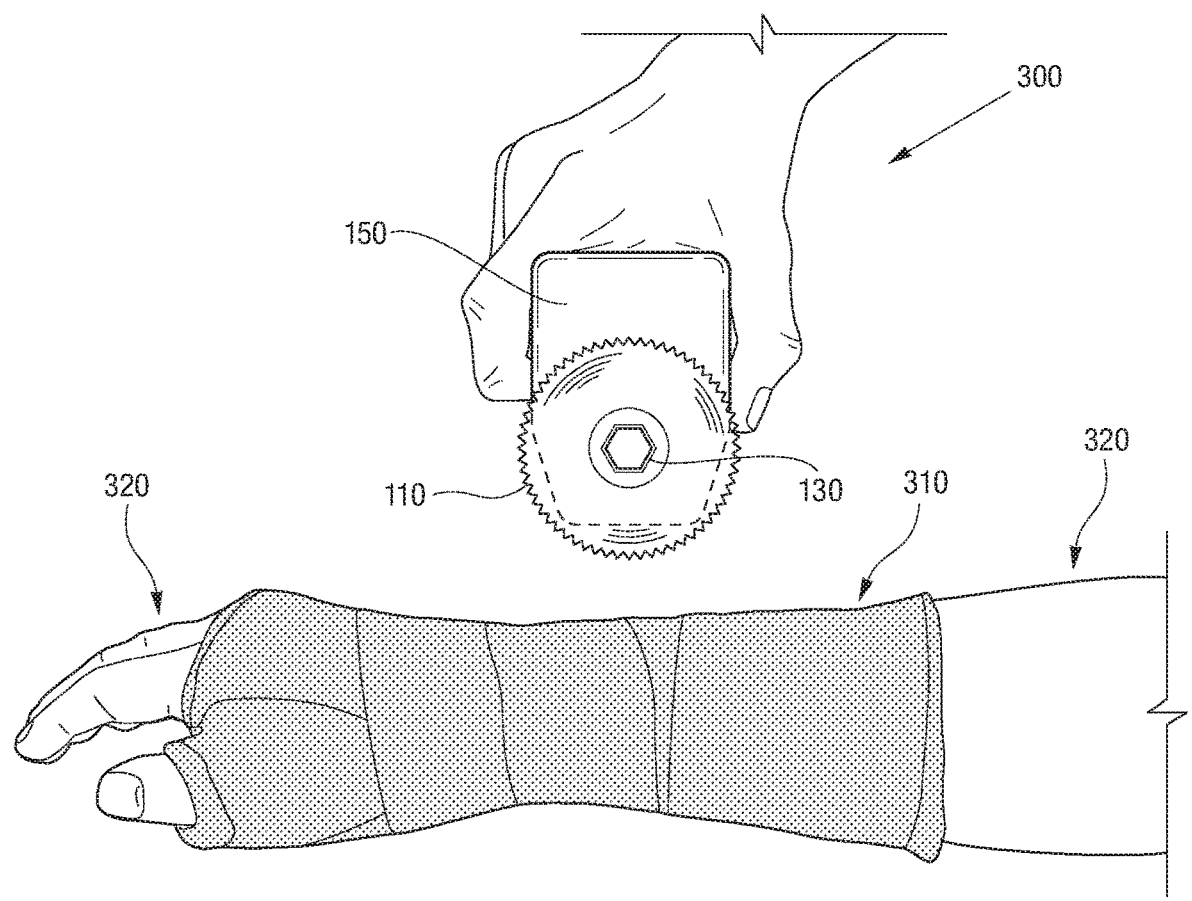
FIG. 8 shows a schematic diagram of the apparatus of the present invention in use.

With reference to FIG. 7, the plurality of temperature sensors 120 may be mounted on the cast saw body 150 and external to the cast saw blade 110.

Having a plurality of temperature sensors 120 provides an advantage over the prior art because, with an oscillating cast saw blade 110, more than one of a plurality of cutting regions 112 of the cast saw blade 110 may be used at different moments to cut a particular cast, which allows the user 300 of the cast saw temperature safety system 100 to give one or more cutting regions 112 of the cast saw blade 110 time in which to cool to a safer temperature, and allows use of more than one cutting region 112 of the cast saw blade 110, as the saw teeth of a particular cutting region 112, at the edge of the cast saw blade 110, dull with use. With the plurality of temperature sensors 120 of the present disclosure, the cast saw temperature safety system 100 monitors multiple cutting regions 112 of the cast saw blade 110, any and all of which may be used for cutting an orthopedic cast 310, and the temperature control system 160 of the cast saw temperature safety system 100 can slow or stop the cast saw blade 110 if one or more of the cutting regions 112, from a plurality of cutting regions 112 of the cast saw blade 110, reaches or exceeds a temperature threshold. While it is possible for a cast saw made with the cast saw temperature safety system 100 of the present invention to safely operate to cut an orthopedic cast 310 while one or more of the cutting regions 112 of the cast saw blade 110 are at or above a temperature threshold, by cutting with a cutting region 112 that is below such a temperature threshold, for patient safety and the safety of the operator of the cast saw—namely, lowering the risk of burns—it has been found advantageous to have operation of such a cast saw temperature safety system 100 be slowed or stopped if any of the cutting regions 112 of the cast saw blade 110 are at or above a temperature threshold established for patient safety. In some embodiments of the present invention, the cast saw temperature safety system 100 can operate with one or more of the cutting regions 112 of the cast saw blade 110 at or above a temperature threshold, provided that the cutting region 112 that is actively cutting is not at or above a temperature threshold. In such embodiments, the cast saw temperature safety system 100 monitors the cutting regions 112 of the cast saw blade 110 to determine which cutting region 112 is actively cutting, by i) monitoring the temperatures of multiple cutting regions 112, where the cast saw temperature safety system 100 can detect that a first cutting region 112 is heating up then it must be being used to cut, and a second (or more) other cutting region 112 of the cast saw blade 110 can be at or above the temperature threshold, and the first cutting region 112 can be used for cutting while the second (or more) cutting region 112 is above the threshold is cooling, and/or ii) monitoring strain on the cast saw blade 110 through the use of a plurality of strain gauges 122. The plurality of strain gauges 122 are, in such embodiments of the present invention, attached to the cast saw blade 110 in one or more of the cutting regions 112, and generate a plurality of strain information, so that the plurality of strain gauges 122 can be used in a method to determine which cutting region 112 of the cast saw blade 110 is actively cutting, and operate to not stop the cutting if the cutting region 112 that is actively cutting is not at or above a temperature threshold. In such embodiments of the present invention, the temperature control system 160 operating to slow or stop the cast saw blade 110 if one or more of the cutting regions 112 reaches or exceeds a temperature threshold, does not operate to slow or stop the cast saw blade 110 if the one or more of the cutting regions 112 that reaches or exceeds a temperature threshold is not the region that is actively cutting. The temperature control system 160 can detect which of the one or more of the cutting regions 112 is the region that is actively cutting, through use of information generated by an accelerometer 162, which accelerometer 162 may be mounted in or on the temperature control system 160, though other positions of the accelerometer 162 are possible, including but not limited to mounted on the cast saw body 150, on the cast saw arbor 130, or on the cast saw blade 110. The accelerometer 162 detects the orientation of the cast saw blade 110 and/or of the cast saw body 150, generates a plurality of orientation information, and conveys the plurality of orientation information to the temperature control system 160. With the plurality of orientation information, and with any available information from the plurality of strain gauges 122, the temperature control system 160 can determine the orientation of the cast saw body 150, and therefore the orientation of the cast saw blade 110, and using that orientation information, can determine which of the one or more of the cutting regions 112 is the region that is actively cutting, typically because best and standard practice in the field is to only cut straight down, though one of skill in the art will see that the temperature control system 160 could be used with types of medical practice for cast removal other than only cutting straight down. The temperature control system 160 can control the operation of the cast saw blade 110, such that the temperature control system 160 does not operate to slow or stop the cast saw blade 110 if the one or more of the cutting regions 112 that reaches or exceeds a temperature threshold is not the region that is actively cutting.

The plurality of temperature sensors 120 may comprise one or more selected from a list comprising thermocouples, resistive temperature devices, thermistors, infrared radiators, lasers, bimetallic devices, liquid expansion devices, optical sensors, fiber Bragg grating optical sensors or other distributed Bragg reflector, thermowells, resistance thermometer, resistance temperature detectors, digital thermal imaging, infrared temperature measurement, or change-of-state devices. Any of these types of temperature sensors 120 may be used, in any combination, whether they are fixedly or movably attached to the cast saw body 150 to be positioned at or near the cast saw blade 110, or be positioned away from the cast saw blade 110, or embedded in or placed on the cast saw blade 110.

The plurality of temperature sensors 120 convey temperature information to the temperature control system 160, by wired or wireless means as previously described, which temperature information may comprise a plurality of temperature readings with one or more readings for each of one or more cutting regions 112 of the cast saw blade 110. The temperature control system 160 processes the plurality of temperature information for the plurality of cutting regions 112 to determine if the temperature of the cast saw blade 110 at a cutting region 112 of the cast saw blade 110 is at or above a threshold temperature, which threshold temperature is set or may be set at a temperature that is considered safe and unlikely to cause a burn to the person wearing the orthopedic cast 310. Based on the plurality of temperature information and the determined temperature of the cast saw blade 110 at least one cutting region 112, the temperature control system 160 sends a control signal to the cast saw motor 140. The temperature control system 160 may cause the cast saw motor 140 to slow or stop, or allow the cast saw motor 140 to remain oscillating at the current speed, or at a higher speed.

The temperature control system 160 may have programmed into it, or otherwise implement, a plurality of modes of controlling the operation of the cast saw motor 140 and thus the cast saw blade 110, in response to the plurality of temperature information from the plurality of temperature sensors 120. The temperature control system 160 may modify the oscillation speed of the cast saw blade 110 to prevent the cast saw blade 110 from reaching a temperature in which the skin of the patient 320 would be burned or would be likely to be burned, such temperature of the cast saw blade 110 being referred to as a temperature threshold or limit, a safe temperature threshold or limit, or a temperature safety threshold or limit.

The temperature control system 160 can be set to control the cast saw temperature safety system 100 by decreasing the oscillation speed of the cast saw blade 110 as the temperature of the cast saw blade 110 overall or in any particular cutting region 112 of the cast saw blade 110 is rising, or shut off or pause the cast saw blade 110 oscillations once a certain cast saw blade 110 safe temperature threshold is reached.

The temperature control system 160 may be controlled by the user 300 to select or set a maximum safe temperature threshold. The temperature control system 160 may have a safety mode in which the cast saw motor 140 and thus cast saw blade 110 will be shut off by the temperature control system 160 at a certain temperature threshold that can be set by the user 300. Another mode of controlling the operation of the cast saw temperature safety system 100 by the temperature control system 160 is a dynamic mode that will decrease the oscillation speed of the cast saw blade 110 as the cast saw blade 110 temperature increases, based on the temperature information from the plurality of temperature sensors 120. As the cast saw blade 110 temperature decreases, the oscillation speed will increase.

Another mode of controlling the operation of the cast saw temperature safety system 100 by the temperature control system 160 may allow the cast saw blade 110 to oscillate at the highest oscillation speed possible without the cast saw blade 110 temperature reaching or exceeding a maximum temperature threshold. The temperature control system 160 may control the cast saw blade 110 oscillations to be continuous or intermittent. The temperature control system 160 may control the cast saw blade 110 at any of a plurality of discrete oscillation speeds selectable by the user 300; such a plurality of oscillation speeds may include, but are not limited to, slow, medium, and high. A fail safe mode for the cast saw temperature safety system 100 can be controlled by the temperature control system 160, in which the temperature control system 160 shuts off or pauses the cast saw blade 110 oscillations if a certain cast saw blade 110 temperature threshold is reached, and may prevent the cast saw blade 110 from oscillating until the cast saw blade 110 temperature is below the temperature threshold, or until the cast saw blade 110 temperature is below the temperature threshold by a certain margin of temperature. The temperature control system 160 may slow the oscillations of the cast saw blade 110 as the temperature information from the plurality of temperature sensors 120 indicates that the temperature of a cutting region 112 of the cast saw blade 110 is approaching a temperature threshold.

The temperature control system 160 may provide one or more warnings to the user 300, with any combination of auditory warnings with an alarm or a tone, visible warnings with lights or a readable display of warning information, tactile feedback with vibrations in the cast saw body 150 or by a pattern of pulsation of the cast saw blade 110, and/or with other warning means to provide the user 300 feedback regarding the temperature of the cast saw blade 110. The temperature control system 160 may provide any combination of the foregoing warnings or information as the temperature of the cast saw blade 110 approaches and/or reaches one or more temperature thresholds. The foregoing warning or warnings can change pitch, volume, frequency, display of information, or tactile feedback to alert the user 300 to the temperature of the cast saw blade 110. A display, which may be incorporated into the temperature control system 160, may show the current temperature of at least one cutting region 112 of the cast saw blade 110. Any of the foregoing types of warnings or displays of information may be implemented with any of the foregoing types of control modes that may be implemented by the temperature control system 160 of the cast saw temperature safety system 100.

With reference to FIG. 5, an embodiment of the cast saw temperature safety system 100 is shown in conjunction with a cast saw burn reduction system 200 which may be used to cool and/or lubricate the cast saw blade 110, so as to lower the temperature of the cast saw blade 110 at one or more cutting regions 112 of the cast saw blade 110. A cast saw burn reduction system 200 may be used with any of the foregoing embodiments of the cast saw temperature safety system 100. With reference to FIG. 3, FIG. 4, FIG. 5, and FIG. 7, a cast saw burn reduction system 200 of the present invention may comprise a cast saw blade 110 with a plurality of cutting regions 112, a cast saw arbor 130, a cast saw motor 140, a cast saw body 150, a coolant 274, and a plurality of coolant applicators 282. The cast saw burn reduction system 200 may further comprise a coolant control system.

The cast saw burn reduction system 200 further comprises coolant components for applying coolant to at least one cutting region 112 of the cast saw blade 110, which components may comprise a coolant reservoir 270, a reservoir cap 272 which may be fastened to close an opening in the coolant reservoir 270, a coolant applicator 276, a coolant pump 278, and a coolant control dial 280. The cast saw burn reduction system 200 coolant components for applying coolant to at least one cutting region 112 of the cast saw blade 110 may further comprise at least one coolant intake 284. The cast saw burn reduction system 200 allows for the user 300 to control or cause to be released or applied onto or at the cast saw blade 110 the coolant 274. The coolant 274 may be released at or onto a plurality of locations on the cast saw blade 110, which locations may be at or near the active cutting region 112 of the cast saw blade 110. Alternatively, or in addition, the cast saw burn reduction system 200 may be programmed to release or apply coolant 274 automatically at or onto a plurality of locations on the cast saw blade 110, which locations may be at or near the active cutting region 112 of the cast saw blade 110.

The coolant 274 may be a coolant for evaporative cooling of the cast saw blade 110, including but not limited to water or isopropyl alcohol, or the coolant 274 may be a coolant for convective heat transport away from the cutting region 112 of the cast saw blade 110, including but not limited to ambient air, or any gas from another source such as compressed air from a tank external to the saw or mounted on the cast saw, that is blown at and over the surface of the cast saw blade 110. Any gas from a compressed tank would have the advantage, for temperature-reduction purposes of the present invention, of cooling as it is released from pressure, increasing its effectiveness at lowering the temperature of the cast saw blade 110. Alternatively, the coolant 274 may be a lubricant, including but not limited to hydrocarbon-based lubricants such as mineral oil or other lubricants, that serves to lower the temperature of at least one cutting region 112 of the cast saw blade 110 by reducing friction between the cast saw blade 110 and the cast. A coolant 274 that is a lubricant may serve to keep the temperature of the cast saw blade 110 from rising, avoiding the need to have it lowered by application of a coolant 274 for evaporative cooling, convective cooling, or other type of cooling. A coolant 274 that is a lubricant may be a lubricant that will spread on the cast saw blade 110 to coat the exterior of the cast saw blade 110 with a film or coating of lubricant, this may be accomplished through the use of a sponge-like material, meaning one that is absorbent of the lubricant, through which the lubricant may be transported and then released out of or from, such that the lubricant is either in contact with or in close proximity to the cast saw blade 110.

In some embodiments of the present invention, it has been found advantageous to have more than one type of coolant 274 applied to a cutting region 112 of the cast saw blade 110; for instance, water or mineral oil may be used as a lubricant, and air may be applied for cooling purposes, in some embodiments of the present invention. In such embodiments of the present invention, there may be present more than one each of one or more of the following components: a coolant reservoir 270, a reservoir cap 272, a coolant 274, a coolant tube 276, a coolant pump 278, a coolant control dial 280, and a coolant intake 284.

In some embodiments of the present invention, the coolant 274 or one of the plurality of coolants 274 (in embodiments with more than one coolant 274) may be applied to only one side of the cast saw blade 110. In other embodiments of the present invention, the coolant 274 may be applied to both sides of the cast saw blade 110.

Where the cast saw burn reduction system 200 comprises a coolant reservoir 270, a reservoir cap 272, a coolant 274, a coolant tube 276, a coolant pump 278, and a coolant control dial 280, the user 300 may reversibly remove the reservoir cap 272 to expose an opening in the coolant reservoir 270, fill the coolant reservoir 270 with coolant 274 and/or remove coolant 274 from the coolant reservoir 270, and secure the reservoir cap 272 to close the coolant reservoir 270. The coolant tube 276 transports coolant 274 from the coolant reservoir 270 to the cast saw blade 110. In some embodiments of the present invention, the coolant tube 276 may split into one or more branches or segments for each side of the cast saw blade 110, so that the coolant 274 may be applied to one or both sides of the cast saw blade 110. Alternatively, the coolant tube 276 may comprise a plurality of discrete tubes or items for transport of one or more coolants 274.

After transport through the coolant tube 276, the coolant 274 is applied by the plurality of coolant applicators 282 to the cast saw blade 110, advantageously, at or near the cutting region 112. The user 300 should, it has been found advantageous, be able to direct the coolant 274 onto a desired location or locations on the cast saw blade 110. If the coolant 274 is a lubricant, the lubricant should advantageously form a film of lubricant between one or both sides of the cast saw blade 110 and the orthopedic cast 310, which reduces the frictional drag between the orthopedic cast 310 and the cast saw blade 110, lowering the risk that the cast saw blade 110 becomes hot enough to burn the patient 320 wearing the orthopedic cast 310. A coolant 274 that is a lubricant should be used in quantities sufficiently small so that it does not significantly moisten the orthopedic cast 310 or the cast padding that is typically used between the patient 320 and the rigid material of the orthopedic cast 310. If the coolant 274 provides evaporative cooling or convective cooling, it should be used in small enough quantities so that it does not drip into and moisten the orthopedic cast 310, or get expelled from the cast saw blade 110 due to the rapid accelerations of the cast saw blade 110 as the cast saw blade 110 oscillates.

The coolant 274 may be applied to the cast saw blade 110 via the coolant tube 276 and the plurality of coolant applicators 282 through the operation of the coolant pump 278, and will be understood by one of skill in the art that one or more types of coolant 274 may be used in a given embodiment of the present invention. The coolant pump 278 impels or pushes the coolant 274 from the coolant reservoir 270 if the coolant 274 is held in the coolant reservoir 270, such as a liquid evaporative coolant or liquid lubricant. If the coolant 274 is ambient air, the coolant pump 278 may impel or push the coolant 274 from the coolant intake 284, which coolant intake 284 is used to gather the ambient air to be used as the coolant 274, through the coolant tube 276 and the plurality of coolant applicators 282 at the cast saw blade 110. In another embodiment of the present invention, ambient air may be used as the coolant 274 by using the coolant pump 278 as a vacuum to draw air through the coolant tube 276, cooling the cast saw blade 110 through the motion of the ambient air over the cast saw blade 110, and having the additional advantage of serving as a vacuum to remove and clean debris from the cutting of the orthopedic cast 310. In embodiments of the invention where the coolant 274 is gas from another source (other than ambient air), the coolant pump 278 may impel or push or release the coolant 274 from the coolant intake 284 or from the coolant reservoir 270, through the coolant tube 276 and the plurality of coolant applicators 282 at the cast saw blade 110. In an embodiment of the present invention where the coolant 274 is a fluid or liquid, the coolant 274 may be applied with the plurality of coolant applicators 282, where the plurality of coolant applicators 282 comprise a sponge-like material, meaning a material that can absorb, transport, and release a fluid coolant 274, in contact with or in close proximity to the cast saw blade 110, where the plurality of coolant applicators 282 are close enough to the cast saw blade 110 that the coolant 274 wicks from the plurality of coolant applicators 282 to the cast saw blade 110. The coolant pump 278 may be a manually actuated component, including but not limited to a bulb or crank to actuate the coolant pump 278 to apply a quantity of coolant 274 to the cast saw blade 110, or the coolant pump 278 may be electrically actuated, to apply a quantity of coolant 274 to the cast saw blade 110. The user 300 may use the coolant control dial 280 to control the quantity of the coolant 274 that is applied per actuation of the coolant pump 278. The coolant control dial 280 may control the pressure of the coolant pump 278 if the coolant pump 278 is electrically actuated, or the aperture of the plurality of coolant applicators 282 if the coolant pump 278 is mechanically actuated, or the pressure in the coolant reservoir 270 if the coolant pump 278 is mechanically actuated. In embodiments of the present invention where the coolant pump 278 is electrically actuated, the coolant control system may be used to automatically apply coolant 274, in one or more ways as described herein, including but not limited to at specific time intervals. In embodiments of the present invention in which the coolant control system is used in conjunction with the temperature control system 160, the coolant control system may be controlled to actuate the coolant pump 278, and thus apply coolant 274 to the cast saw blade 110, when the temperature control system 160 indicates that the temperature information is at or above a certain threshold value for the temperature of a cutting region 112 of the cast saw blade 110. The temperature control system 160 and the coolant control system may be separate or may be integrated together as a component or set of components of the cast saw temperature safety system.

Certain embodiments of the present invention were described above. From the foregoing it will be seen that this invention is one well adapted to attain all the ends and objects set forth above, together with other advantages, which are obvious in and inherent to the inventive apparatus disclosed herein. It will be understood that certain features and sub-combinations are of utility and may be employed without reference to other features and sub-combinations. It is expressly noted that the present invention is not limited to those embodiments described above, but rather the intention is that additions and modifications to what was expressly described herein are also included within the scope of the invention. Moreover, it is to be understood that the features of the various embodiments described herein are not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

Accordingly, what is claimed is:

1. A method of controlling an operation of a cast saw temperature safety system, wherein the cast saw temperature safety system comprises a cast saw blade, a plurality of temperature sensors, a cast saw arbor to which the cast saw blade is attached, a cast saw motor operably connected to the cast saw arbor, a cast saw body enclosing the cast saw motor, and a temperature control system which controls the cast saw motor to oscillate; the cast saw blade comprising a plurality of cutting regions and a plurality of strain gauges; the method comprising:
   the cast saw temperature safety system having a temperature threshold for the plurality of cutting regions;
   the cast saw temperature safety system monitoring temperature information for each of one or more of the plurality of cutting regions;
   the temperature control system sending a control signal to the cast saw motor; and
   the temperature control system operates to slow or stop the cast saw blade if one or more of the cutting regions reaches or exceeds the temperature threshold;

except that the temperature control system does not operate to slow or stop the cast saw blade if the one or more of the cutting regions that reaches or exceeds the temperature threshold is or are not actively cutting; and wherein whether the one or more of the cutting regions that reaches or exceeds the temperature threshold is or are actively cutting is determined by a plurality of strain information from the plurality of strain gauges.

2. A method of controlling an operation of a cast saw temperature safety system, wherein the cast saw temperature safety system comprises a cast saw blade, a plurality of temperature sensors, an accelerometer, a cast saw arbor to which the cast saw blade is attached, a cast saw motor operably connected to the cast saw arbor, a cast saw body enclosing the cast saw motor, and a temperature control system which controls the cast saw motor to oscillate; the cast saw blade comprising a plurality of cutting regions; the method comprising:

the cast saw temperature safety system having a temperature threshold for the plurality of cutting regions;

the cast saw temperature safety system monitoring temperature information for each of one or more of the plurality of cutting regions;

the temperature control system sending a control signal to the cast saw motor; and the temperature control system operating to slow or stop the cast saw blade if one or more of the cutting regions reaches or exceeds the temperature threshold; and wherein the temperature control system determines that the one or more of the cutting regions that reaches or exceeds the temperature threshold is or are not actively cutting based on a plurality of orientation information from the accelerometer.

* * * * *